United States Patent [19]

Heilman et al.

[11] Patent Number: 4,662,377
[45] Date of Patent: May 5, 1987

[54] CARDIOVERTING METHOD AND APPARATUS UTILIZING CATHETER AND PATCH ELECTRODES

[75] Inventors: Marlin S. Heilman, Gibsonia, Pa.; Stanley M. Bach, Jr., St. Paul, Minn.

[73] Assignee: Mieczyslaw Mirowski, Owings Mills, Md.

[21] Appl. No.: 795,781

[22] Filed: Nov. 7, 1985

[51] Int. Cl.⁴ .............................................. A61N 1/04
[52] U.S. Cl. .............................. 128/419 D; 128/419 P; 128/786
[58] Field of Search ............... 128/419 D, 419 P, 783, 128/784, 785, 786, 705, 642, 695, 696

[56] References Cited

U.S. PATENT DOCUMENTS

| Re. 27,757 | 9/1973 | Mirowski | 128/419 D |
|---|---|---|---|
| 2,985,172 | 5/1961 | Jones | 128/784 |
| 3,664,347 | 5/1972 | Harmjanz | 128/786 |
| 3,706,313 | 12/1972 | Milani et al. | 128/419 D |
| 3,866,615 | 2/1975 | Hewson | 128/419 D |
| 3,915,174 | 10/1975 | Preston | 128/419 P |
| 3,942,536 | 3/1976 | Mirowski et al. | 128/419 D |
| 3,995,623 | 12/1976 | Blake et al. | 128/419 P |
| 4,010,755 | 3/1977 | Preston | 128/419 P |
| 4,030,509 | 6/1977 | Heilman et al. | 128/419 D |
| 4,161,952 | 7/1979 | Kinney et al. | 128/786 |
| 4,270,549 | 6/1981 | Heilman | 128/784 |
| 4,289,136 | 9/1981 | Halvorsen | 128/419 P |
| 4,300,567 | 11/1981 | Kolenik et al. | 128/419 D |
| 4,407,288 | 10/1983 | Langer et al. | 128/419 PG |
| 4,444,195 | 4/1984 | Gold | 128/786 |
| 4,548,203 | 10/1985 | Jacker, Jr. et al. | 128/784 |
| 4,603,705 | 8/1986 | Speicher et al. | |

FOREIGN PATENT DOCUMENTS

| 2853253 | 6/1980 | Fed. Rep. of Germany | 128/419 D |
|---|---|---|---|
| 3300672 | 7/1984 | Fed. Rep. of Germany | 128/786 |
| 2504394 | 10/1982 | France | 128/419 P |
| 8002801 | 12/1980 | PCT Int'l Appl. | 128/786 |
| 2157178 | 10/1985 | United Kingdom | |
| 810212 | 3/1981 | U.S.S.R. | 128/695 |

OTHER PUBLICATIONS

Cardiac Shocks—Space-Age Help for the Heart, Aug. 1980, p. 80 of Time.

Jan.-Feb. 1986 *Medical Instrumentation*, vol. 20, No. 1, pp. 36–39, "Optimization of Epicardial Electrode Size and Implant Site for Reduced Sequential Pulse Defibrillation Thresholds".

*Primary Examiner*—Edward M. Coven
*Attorney, Agent, or Firm*—Fleit, Jacobson, Cohn & Price

[57] ABSTRACT

A novel electrode apparatus and method for use with an automatic implantable cardioverter/defibrillator. The electrode apparatus includes a catheter electrode intravenously positioned within the heart of a patient wherein one electrode, defined by the catheter, is within the right ventricle and a second electrode, defined by the catheter, spaced from the first electrode, is within the superior vena cava. A third electrode, in the form of a flexible, substantially planar patch, is subcutaneously positioned outside the thoracic cavity proximate to the apex of the left ventricle. The third electrode is electrically connected with the second electrode of the catheter. The electrode arrangement can be implanted without opening of the thoracic cavity by intravenously placing the catheter electrode within the heart of a patient and subcutaneously implanting the patch electrode between the skin and the thoracic cavity. The automatic implantable cardioverter/defibrillator senses life-threatening arrhythmic conditions of the heart and issues at least one cardioverting or defibrillating pulse that is applied between the electrode positioned within the right ventricle and the electrode pair comprising the electrodes positioned within the superior vena cava and subcutaneously adjacent the apex of the left ventricle.

10 Claims, 1 Drawing Figure

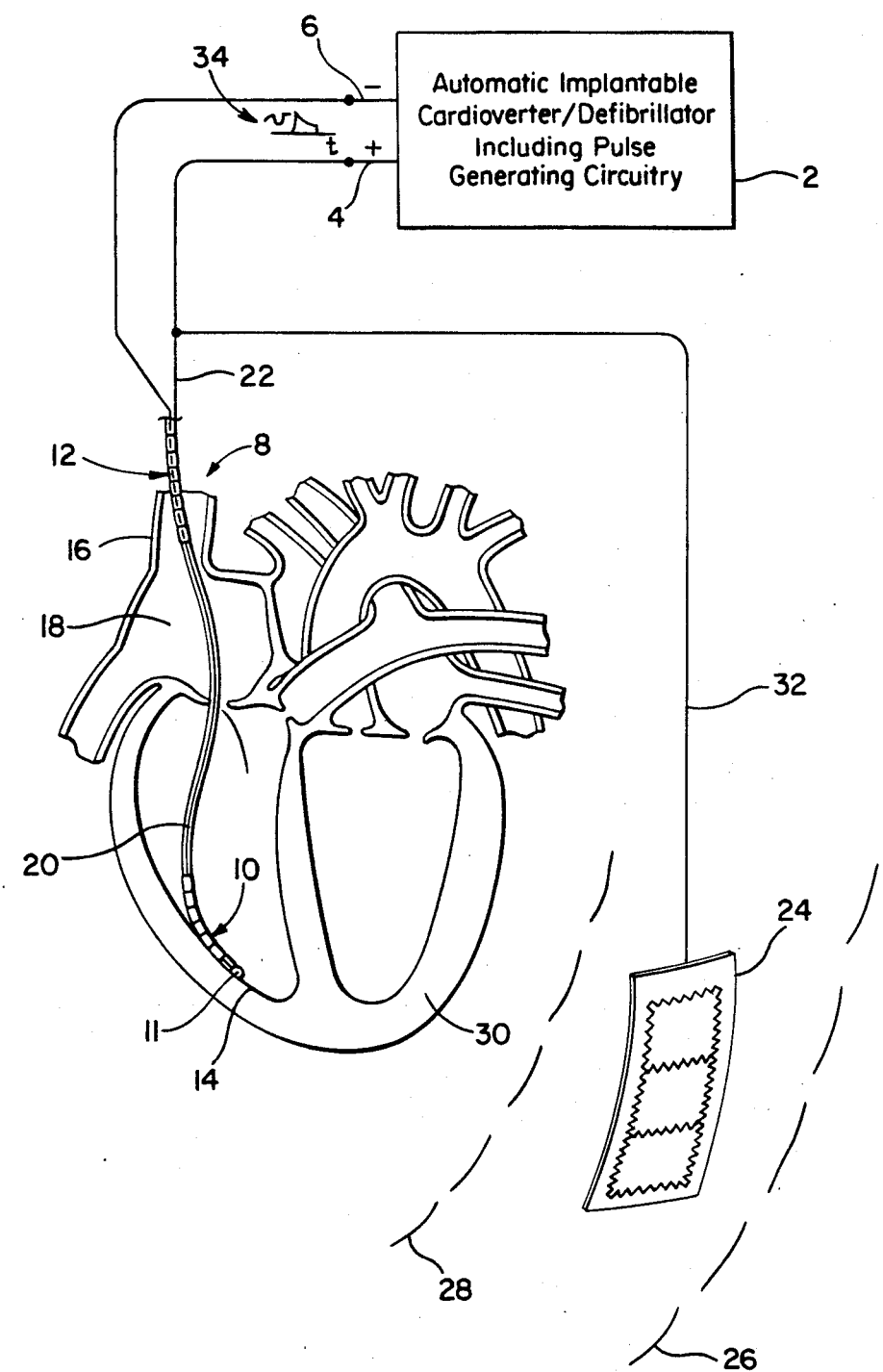

CARDIOVERTING METHOD AND APPARATUS UTILIZING CATHETER AND PATCH ELECTRODES

BACKGROUND OF THE INVENTION

The present invention relates to a novel electrode arrangement and method for an automatic implantable cardioverter/defibrillator. The electrode arrangement includes a catheter electrode intravenously positioned within the heart of a patient wherein one electrode on the catheter is within the right ventricle and a second electrode on the catheter is within the superior vena cava. A third electrode, in the form of a flexible, substantially planar patch, is subcutaneously positioned outside the thoracic cavity proximate to the apex of the left ventricle. The third electrode is electrically connected with the second electrode of the catheter.

Approximately 250,000 Americans under the age of 65 die yearly from a condition termed "sudden cardiac death". In the vast majority of these cases, the cause of death is ventricular tachycardia and/or ventricular fibrillation. An automatic implantable cardioverting-/defibrillating device has been developed and shown to be effective in preventing sudden cardiac death from these causes. See, for example, U.S. Pat. No. 4,407,288

As used herein, the term cardioversion may be generally defined as the correction of either ventricular tachycardia or ventricular fibrillation by the discharge of electrical energy into the heart (0.1–40 joules when discharged through internal electrodes). Ventricular tachycardia is an abnormally rapid heart rate (120-180 beats per minute) originating in the the heart's main pumping chambers (ventricles) which is regular in periodicity and oftentimes is life threatening to the patient. Ventricular fibrillation is generally a more rapid heartbeat disorder, disorganized and irregular, or non-periodic, and is fatal unless corrected within minutes by the discharge of electrical energy through the heart. More specific medical terminology often uses the term cardioversion to mean the synchronized delivery of an electrical shock to the heart to correct ventricular tachycardia. Defibrillation, then, is often referred to as the non-synchronized delivery of electrical energy to the heart to correct ventricular fibrillation. Internal cardioversion is usually effective with 0.1 to 3 joules of electrical energy when delivered in synchronism with the electrical heartbeat. Internal defibrillation requires 5 to 30 or more joules of electrical energy, depending largely on the electrode system used.

Over the years, a number of different types of electrode systems have been suggested for use with an automatic implantable cardioverter/defibrillator. For example, U.S. Pat. No. Re. 27,757 describes an electrode arrangement whereby one electrode is formed on the distal end of an intravascular catheter that is positioned within the right ventricle, whereas the second electrode is positioned on the surface of the chest or sutured under the skin of the chest wall or directly to the ventricular myocardium. U.S. Pat. No. 3,942,536 discloses a catheter electrode system wherein both electrodes are on a single intravascular catheter. The distal electrode is wedged in the apex of the right ventricle and the proximal electrode is immediately superior to the right atrium.

An improved intravascular catheter electrode system is described in copending U.S. Pat. No. 4,603,705 filed on May 4, 1984, issued on Aug. 5, 1986 and assigned to the same assignee as the present invention. There, the proximal electrode is located in the superior vena cava and the distal electrode is in the right ventricle. A sensing and pacing electrode is also provided at the distal tip of the catheter. The first two electrodes constitute the anode and cathode of the cardioverting/defibrillating electrode pair. The tip electrode is used for sensing heart rate and pacing the heart. Using this single catheter system, energies required to defibrillate the human heart have been found to vary between 5-40 joules, but in some 40-50% of patients, even the higher energies may be insufficient to defibrillate the heart. Thus, although this improved catheter electrode system has many advantages, such as the capability of being installed without surgically invading the thoracic cavity, it has been found to have somewhat limited effectiveness in terminating ventricular fibrillation.

Various other electrode arrangements have also been employed. In U.S. Pat. No. 4,030,509, the implantable electrode system includes, among others, a flexible apex electrode designed to surround the apex of the heart, and various flexible base electrodes designed to surround the base of the heart.

The electrodes presently used by the automatic implantable cardioverter/defibrillator consist of one defibrillating electrode placed in the superior vena cava/right atrial region, and a second flexible, conformal, defibrillating electrode placed on the outside of the heart, typically over the lateral wall of the left ventricle. See, U.S. Pat. Nos. 4,161,952 and 4,270,549. Placement of the first electrode can be accomplished by the insertion of a catheter-mounted electrode into one of the veins outside of the thorax and sliding the catheter electrode centrally into the venous system until the electrode portion is within the thorax and located at the junction of the superior vena cava and right atrium. Thus, for the placement of this electrode, it is not necessary to surgically enter the thorax. For the second electrode, however, it is necessary to make one of a variety of surgical incisions to open the thoracic cavity in order to place the electrode over the left ventricle of the heart. Each of these surgical approaches has serious disadvantages. Two such approaches involve extensive surgery and substantial patient recovery time with a cost currently between $8-12,000. These approaches consist of splitting the sternum (breastbone) or alternatively opening a space between the ribs in order to gain access to the surface of the heart. A third approach involves making a smaller incision under the xiphoid process of the sternum, which is simpler from a surgical point of view, but still involves entering the thoracic cavity. Moreover, this approach sometimes does not allow convenient positioning of the left ventricular electrode.

With providers of health care becoming increasingly cost conscious due to limited payment resources, it is more and more important to reduce surgical costs in order that life-saving therapies can be made broadly available. Thus, to both reduce the morbidity associated with the surgery of defibrillator electrode implantation and to reduce the cost, it is highly desirable to have a means of electrode implantation which does not involve the surgical opening of the thoracic cavity.

SUMMARY OF THE INVENTION

The present invention is an improved electrode placement method and apparatus for an automatic implantable cardioverter/defibrillator that does not require the surgical opening of the thoracic cavity. The electrode system includes an intravascular catheter insertable within the heart of a patient having a first electrode adjacent the distal end of the catheter and a second electrode positioned at the proximal end of the catheter. This catheter electrode is of the type described in copending U.S. Pat. No. 4,603,705, filed on May 4, 1984, incorporated herein by reference. Associated with this catheter electrode is a third electrode, in the form of a flexible patch electrode, that is placed subcutaneously outside of the thoracic cavity (rib cage), but proximate to the apex of the left ventricle. This third patch electrode is electrically connected (i.e. in common) with the second electrode of the catheter, the latter of which is positioned in the superior vena cava/right atrium region. The first, or distal, electrode of the catheter, completes the cardioverting/defibrillating circuit. A pulse, or shock, of electrical energy is discharged between the first electrode and the combined second electrode/patch electrode to result in a more efficient depolarization of the heart tissue. Indeed, in animals (dogs), the novel electrode arrangement has been found to significantly lower (by 25-33%) the electrical energy required to defibrillate the heart. The same improved result is expected in the human heart.

It is thus an object of the present invention to provide a new and improved electrode arrangement for an automatic implantable cardioverter/defibrillator that does not require the surgical opening of the thoracic cavity. It is further an object of the present invention to provide a new and improved electrode system that requires lesser energy levels to effectively cardiovert or defibrillate an ailing heart.

Further, it is an object of the present invention to provide an automatic implantable cardioverter/defibrillator system with an implantable electrode arrangement including an intravascular catheter electrode having a first electrode adjacent the distal end of the catheter for positioning in the right ventricle and a second electrode of the catheter, spaced from the first electrode, for positioning in the superior vena cava region. This catheter electrode is used in conjunction with a subcutaneous patch electrode, positioned outside the thoracic cavity proximate to the apex of the left ventricle. The patch electrode is electrically connected to the second electrode of the catheter. Thus, the first, or distal, electrode is connected to one terminal of an implantable pulse generator whereas the second and patch electrodes are connected to a second terminal of the pulse generator.

It is also an object of the present invention to provide a method for automatically cardioverting/defibrillating the heart of a patient by detecting an arrhythmic condition and automatically applying a voltage pulse of a magnitude sufficient to restore normal cardiac rhythm between a first electrode located within the right ventricle of the heart and a pair of electrodes, one of which is positioned in the superior vena cava region and the other of which is positioned adjacent the apex of the left ventricle outside the thoracic cavity.

Still further, it is an object of the present invention to provide a method of implanting electrodes for use in an automatic implantable cardioverter/defibrillator without surgically opening the thoracic cavity. The method includes the steps of intravenously inserting a cathether having first and second electrodes such that the first electrode is within the right ventricle and the second is within the superior vena cava, subcutaneously placing a patch electrode outside the thoracic cavity, and electrically connecting the second and patch electrodes together.

These and other objects of the present invention will be apparent when reference is made to the following detailed description and drawing.

BRIEF DESCRIPTION OF THE DRAWING

The sole FIGURE of the drawing includes the novel electrode arrangement of the present invention in conjunction with an automatic implantable cardioverter/defibrillator system.

DETAILED DESCRIPTION OF A PREFERRED EMBODIMENT

With the reference to the sole FIGURE of the drawing, an automatic implantable cardioverter/defibrillator 2, such as the type described in U.S. Pat. No. 4,407,298, is implantable within the abdominal region of the patient and is coupled with electrodes associated with the heart of the patient. The automatic implantable cardioverter/defibrillator 2 includes sensing and detecting circuitry, as well as pulse generating circuitry, the output of the latter coupled to the implantable electrodes. The cardioverter/defibrillator 2 senses an arrhythmic condition of the heart and, in response thereto, issues or emits cardioverting or defibrillating pulses to the heart, through the implantable electrodes. The cardioverter/defibrillator includes output terminals comprised of an anode 4 and a cathode 6.

Coupled to the cardioverter/defibrillator 2 is a catheter electrode arrangement. The catheter electrode may be identical to that described in copending U.S. Pat. No. 4,603,705, filed on May 4, 1984, incorporated herein by reference. As described in the copending application, the catheter electrode 8 is a flexible electrode that includes a distal portion 10 (sometimes called herein a distal electrode) formed of a conductive spring electrode defined by the perimeter of the catheter and a proximal portion 12 (or proximal electrode) similarly formed of a conductive spring electrode defined by the catheter. The spring electrodes at the distal and proximal portions 10,12 are close-wound electrically conductive-wires, preferably wound to approximately 20 turns per inch. This provides a continuous electrically conductive surface which maintains its flexibility while still lowering the impedance of the electrodes and thus permitting more current to be delivered. Other electrode configurations may be employed, such as ring-type electrodes.

The catheter electrode 8 is inserted intravenously to a position such that the distal electrode 10 is positioned in the right ventricular apex 14 of the heart and the proximal electrode 12 is positioned in the superior vena cava region 16 of the heart. It should be appreciated that, as the term is used herein, the superior vena cava 16 may also include portions of the right atrium 18. That is, the positioning of the proximal electrode 12 may be partially within the right atrium 18 rather than entirely within the superior vena cava 16, depending upon the dimensions of the patient's heart.

The distal electrode 10 is electrically connected, via a conductor 20 that extends along the length of the catheter 8 to the cathode terminal 6 of the cardioverter/defibrillator. The proximal electrode is similarly connected by a conductor 22 to the anode 4 of the cardioverter/defibrillator. The distal and proximal electrodes are electrically isolated from each other.

As described in the incorporated patent the electrical surface area of the distal electrode 10 is approximately in the range of 300 to 500 sq. mm. Other surface areas might be chosen. Further, the spacing between the rearwardmost portion of the distal electrode 10 and the forwardmost portion of the proximal electrode 12 is approximately 8 to 14 cm. Such a distance is chosen so that, for the majority of human heart sizes, the distal electrode 10 is within the right ventricular apex and the proximal electrode 12 is in the superior vena cava/right atrium region.

As also described in the incorporated patent a distal sensing and pacing tip electrode 11 may be included on the catheter. The distal tip 11, in conjunction with the distal electrode 10, provides sensing of the heart rate as well as pacing functions. The tip 11 is electrically insulated from the distal electrode 10. Moreover, the distal electrode 10 and the proximal electrode 12 may be used as an input to a probability density function (PDF) sensing circuit within the cardioverter/defibrillator 2, whereby a PDF signal, indicative of an arrhythmia condition, may be detected. (During the sensing of the PDF signal from the electrodes 10, 12, the patch electrode 24, to be described below, may be electrically isolated.) Thus, the implantable cardioverter/defibrillator 2 senses heart rate via electrodes 10, 11, senses PDF signals via electrodes 10, 12 and issues cardioverting/defibrillating pulses, via electrodes 10, 12 and 24 (in a manner to be described) when the sensed heart rate/PDF signals satisfy certain predetermined criteria.

A flexible patch electrode 24 is electrically connected to proximal electrode 12, and is subcutaneously positioned outside the thoracic cavity. That is, the patch electrode 24 is positioned between the skin 26 and the rib cage 28. This subcutaneous implantation does not require any opening of the rib cage, or thoracic cavity 28.

The patch electrode is positioned proximate to the left ventricular apex 30 of the heart. Preferably, the patch electrode is positioned at the point of maximum impulse of the heart. This point is determined empirically by physically detecting where the maximum heart beat can be felt or heard.

The patch electrode 24 may be similar to that depicted in U.S. Pat. No. Des. 273,514. The patch electrode is a flexible, conformal, generally planar electrode having a metallic mesh on the surface facing the heart, and flexible insulating material on its rear side. The patch electrode may have a surface area of 13.5 sq.cm. although other surface areas may be effectively employed depending upon the energy levels required.

As depicted in the drawing, the path electrode 24 is connected, via a conductor 32, to the conductor line 22 which connects the proximal electrode 12 to the anode 4 of the pulse generator 2. It is only necessary that the patch electrode be electrically connected, i.e. connected in common, with the proximal electrode 12; such connection could be made at the automatic implantable cardioverter/defibrillator directly or at any point along the line 22 between the automatic implantable cardioverter/defibrillator and the proximal electrode 12.

In operation, the automatic implantable cardioverter/defibrillator 2, after detecting a life-threatening abnormal heart rhythm, will issue a cardioverting or defibrillating pulse through its pulse generator section. At least one high energy pulse or shock is issued to the implantable electrodes by providing a voltage pulse across the distal electrode 10 and the combination of the proximal electrode 12 with the patch electrode 24. Preferably the high energy pulse is an exponentially decaying truncated voltage, as is depicted in the drawing at 34. As a result, an electrical field is created across the heart that more effectively depolarizes the heart using electrical energies 25-33% lower than would be effective solely using the catheter electrode 8. If unsuccessful, additional pulses may be issued, which may be at increased energy levels.

Above, a specific embodiment of the present invention has been described. It should be appreciated, however, that this description has been given for purposes of illustration only, and is in no way intended to limit the scope of the present invention. Rather, it is the intention that the present invention be limited only as defined in the appended claims.

What is claimed is:

1. In an automatic implantable cardioverter/defibrillator system for delivering electrical shocks to the heart of a patient to restore normal cardiac rhythm, the system including a pulse generator means, having positive and negative electrical output terminals, for generating an electrical shock to implantable electrodes, the improvement comprising:

an intravascular catheter insertable within the heart of a patient having a first electrode defined by the catheter for positioning in the right ventricle, and a second electrode defined by the catheter, spaced from the first electrode, for positioning in the superior vena cava region;

a subcutaneous patch electrode electrically connected with said second electrode of the intravascular catheter, for positioning subcutaneously outside the thoracic cavity proximate to the apex of the left ventricle; and a first electrical conducting means for electrically connecting said first electrode with one of said positive and negative electrical output terminals of said pulse generator means and a second electrical conducting means for electrically connecting both said second electrode and said subcutaneous patch electrode with the other of said positive and negative electrical output terminals of said pulse generator means.

2. The implantable cardioverter/defibrillator system as claimed in claim 1 wherein said pulse generator means generates at least one high energy shock to the implantable electrodes to create an electrical field across the heart between the first electrode and the combined second and subcutaneous patch electrodes.

3. The implantable cardioverter/defibrillator of claim 1 wherein said first and second electrodes are defined by closely-wound electrically conductive wire about the perimeter of the catheter.

4. The implantable cardioverter/defibrillator of claim 1 wherein said patch electrode comprises a substantially planar, flexible patch, one surface formed of metallic mesh, for positioning facing the left ventricle, the opposite surface formed of electrically insulative material.

5. The implantable cardioverter/defibrillator of claim 1 wherein said catheter further includes a third electrode defined at the distal tip of said catheter, wherein said first and third electrodes provide a sensing input to the cardioverter/defibrillator and a pacing pulse output to the heart.

6. A method of automatically cardioverting/defibrillating the heart of a patient comprising the steps of:
   detecting an arrhythmic condition of the heart;
   automatically applying a voltage pulse of a predetermined magnitude to restore normal cardiac rhythm concurrently between a first electrode located within the right ventricle of the heart and both ones of a pair of electrodes, one of said pair positioned within the superior vena cava region of the heart, the other of said pair positioned proximate to the left ventricular apex outside the thoracic cavity.

7. The method of claim 6 wherein the other of said pair of electrodes is positioned subcutaneously and proximate to an empirically determined point of maximal detection of the heart rate.

8. The method of claim 6 wherein said step of automatically applying a voltage pulse comprises applying an exponentially decaying voltage pulse.

9. The method of claim 8 wherein said step of automatically applying a voltage pulse comprises applying a truncated exponentially decaying voltage pulse.

10. A method of implanting electrodes within and adjacent the heart of a patient for use with an automatic implantable cardioverter/defibrillator without surgically opening the thoracic cavity, comprising the steps of:
    intravenously inserting a catheter having a first electrode adjacent the distal end of the catheter and a second electrode adjacent the proximal end of the catheter such that the first electrode is within the right ventricle adjacent the right ventricular apex of the heart and the second electrode is in the region of the superior vena cava;
    subcutaneously placing a patch electrode outside the thoracic cavity proximate to the apex of the left ventricle; and
    electrically connecting both of the second electrode and the patch electrode together.

* * * * *